(12) United States Patent
Hall et al.

(10) Patent No.: US 9,095,683 B2
(45) Date of Patent: Aug. 4, 2015

(54) MEDICAL COMPONENT INSERTION DEVICE INCLUDING A RETRACTABLE NEEDLE

(75) Inventors: John W. Hall, North Salt Lake, UT (US); Ryan C. Patterson, Farmington, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 170 days.

(21) Appl. No.: 13/405,096

(22) Filed: Feb. 24, 2012

(65) Prior Publication Data

US 2012/0220942 A1    Aug. 30, 2012

Related U.S. Application Data

(60) Provisional application No. 61/446,817, filed on Feb. 25, 2011.

(51) Int. Cl.
*A61M 5/178* (2006.01)
*A61M 25/06* (2006.01)
*A61M 29/00* (2006.01)

(52) U.S. Cl.
CPC ............ *A61M 25/0606* (2013.01); *A61M 29/00* (2013.01); *A61M 25/0631* (2013.01)

(58) Field of Classification Search
CPC ............ A61M 25/0606; A61M 29/00; A61M 25/0631
USPC ........................................ 604/164.01–166.01
See application file for complete search history.

(56) References Cited

U.S. PATENT DOCUMENTS

| | | |
|---|---|---|
| 3,185,151 A | 5/1965 | Czorny |
| 3,297,030 A | 1/1967 | Czorny et al. |
| 3,500,828 A | 3/1970 | Podhora |
| 3,589,361 A | 6/1971 | Loper et al. |
| 3,592,192 A | 7/1971 | Harautuneian |

(Continued)

FOREIGN PATENT DOCUMENTS

| | | |
|---|---|---|
| CN | 102939129 A | 2/2013 |
| EP | 747075 A2 | 12/1996 |

(Continued)

OTHER PUBLICATIONS

Access Scientific, The PICC Wand® Product Data Sheet, Revision F, May 22, 2012.

(Continued)

*Primary Examiner* — Theodore Stigell
*Assistant Examiner* — Benjamin Koo
(74) *Attorney, Agent, or Firm* — Rutan & Tucker, LLP

(57) ABSTRACT

An insertion device for use in assisting with the placement of a medical device within the body of a patient is disclosed. For example, the insertion device can be employed to assist with the placement of an introducer, which provides a conduit for insertion of a catheter into the body. In one embodiment, the insertion device comprises a needle that is removably disposed within a bore defined by the medical device, and a needle retraction assembly. The needle retraction assembly can position the needle in any one of a first position wherein a distal tip of the needle is disposed a predetermined distance distal to a distal end of the medical device, a second position wherein the needle distal tip is disposed distal but proximate to the distal end of the medical device, and a third position wherein the needle distal tip is retracted within the medical device bore.

6 Claims, 13 Drawing Sheets

(56) References Cited

U.S. PATENT DOCUMENTS

| | | |
|---|---|---|
| 3,682,173 A | 8/1972 | Center |
| 3,921,631 A | 11/1975 | Thompson |
| 3,995,628 A | 12/1976 | Gula et al. |
| 4,079,738 A | 3/1978 | Dunn et al. |
| 4,354,491 A | 10/1982 | Marbry |
| 4,417,886 A | 11/1983 | Frankhouser et al. |
| 4,581,019 A | 4/1986 | Curelaru et al. |
| D287,877 S | 1/1987 | Holewinski et al. |
| 4,728,322 A | 3/1988 | Walker et al. |
| 4,772,267 A | 9/1988 | Brown |
| 4,781,703 A | 11/1988 | Walker et al. |
| 4,792,531 A | 12/1988 | Kakihana |
| 4,826,070 A | 5/1989 | Kakihana |
| 4,828,547 A | 5/1989 | Sahi et al. |
| 4,834,708 A | 5/1989 | Pillari |
| 4,840,613 A | 6/1989 | Balbierz |
| 4,840,622 A | 6/1989 | Hardy |
| 4,846,812 A | 7/1989 | Walker et al. |
| 4,869,259 A | 9/1989 | Elkins |
| D304,079 S | 10/1989 | McFarlane |
| 4,871,358 A | 10/1989 | Gold |
| 4,883,699 A | 11/1989 | Aniuk et al. |
| 4,894,052 A | 1/1990 | Crawford |
| 4,906,956 A | 3/1990 | Kakihana |
| 4,911,691 A | 3/1990 | Aniuk et al. |
| 4,913,704 A | 4/1990 | Kurimoto |
| 4,955,863 A | 9/1990 | Walker et al. |
| 4,994,042 A | 2/1991 | Vadher |
| 4,994,047 A | 2/1991 | Walker et al. |
| 5,009,642 A | 4/1991 | Sahi |
| 5,019,048 A | 5/1991 | Margolin |
| 5,019,049 A | 5/1991 | Haining |
| D318,733 S | 7/1991 | Wyzgala |
| 5,034,347 A | 7/1991 | Kakihana |
| 5,061,254 A | 10/1991 | Karakelle et al. |
| 5,078,694 A | 1/1992 | Wallace |
| 5,093,692 A | 3/1992 | Su et al. |
| 5,098,395 A | 3/1992 | Fields |
| 5,108,375 A | 4/1992 | Harrison et al. |
| 5,108,376 A | 4/1992 | Bonaldo |
| 5,112,312 A | 5/1992 | Luther |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,156,596 A | 10/1992 | Balbierz et al. |
| 5,158,544 A | 10/1992 | Weinstein |
| 5,186,168 A | 2/1993 | Spofford et al. |
| 5,186,712 A | 2/1993 | Kelso et al. |
| 5,190,528 A | 3/1993 | Fonger et al. |
| 5,192,301 A | 3/1993 | Kamiya et al. |
| 5,195,974 A | 3/1993 | Hardy |
| 5,215,527 A | 6/1993 | Beck et al. |
| 5,217,435 A | 6/1993 | Kring |
| 5,219,335 A | 6/1993 | Willard et al. |
| 5,225,369 A | 7/1993 | Su et al. |
| 5,226,899 A | 7/1993 | Lee et al. |
| D338,955 S | 8/1993 | Gresl et al. |
| 5,257,980 A | 11/1993 | Van Antwerp et al. |
| 5,297,546 A | 3/1994 | Spofford et al. |
| 5,312,361 A | 5/1994 | Zadini et al. |
| 5,352,205 A | 10/1994 | Dales et al. |
| 5,358,796 A | 10/1994 | Nakamura et al. |
| 5,368,661 A | 11/1994 | Nakamura et al. |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,419,766 A | 5/1995 | Chang et al. |
| 5,431,506 A | 7/1995 | Masunaga |
| 5,454,785 A | 10/1995 | Smith |
| 5,458,658 A | 10/1995 | Sircom |
| 5,480,389 A * | 1/1996 | McWha et al. .......... 604/165.02 |
| 5,482,395 A | 1/1996 | Gasparini |
| 5,484,419 A | 1/1996 | Fleck |
| 5,507,300 A | 4/1996 | Mukai et al. |
| 5,522,807 A | 6/1996 | Luther |
| 5,531,701 A | 7/1996 | Luther |
| 5,533,988 A | 7/1996 | Dickerson et al. |
| 5,554,136 A | 9/1996 | Luther |
| 5,562,631 A | 10/1996 | Bogert |
| 5,562,633 A | 10/1996 | Wozencroft et al. |
| 5,569,202 A | 10/1996 | Kovalic et al. |
| 5,569,217 A | 10/1996 | Luther |
| 5,591,194 A | 1/1997 | Berthiaume |
| 5,599,291 A | 2/1997 | Balbierz et al. |
| 5,613,663 A | 3/1997 | Schmidt et al. |
| 5,634,475 A | 6/1997 | Wolvek |
| 5,634,913 A | 6/1997 | Stinger |
| 5,651,772 A | 7/1997 | Arnett |
| 5,674,241 A | 10/1997 | Bley et al. |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,702,369 A | 12/1997 | Mercereau |
| 5,725,503 A | 3/1998 | Arnett |
| 5,730,150 A | 3/1998 | Peppel et al. |
| 5,738,660 A | 4/1998 | Luther |
| 5,743,882 A | 4/1998 | Luther |
| 5,743,888 A | 4/1998 | Wilkes et al. |
| 5,749,371 A | 5/1998 | Zadini et al. |
| 5,755,693 A | 5/1998 | Walker et al. |
| 5,762,630 A | 6/1998 | Bley et al. |
| 5,762,636 A | 6/1998 | Rupp et al. |
| 5,765,682 A | 6/1998 | Bley et al. |
| 5,807,342 A | 9/1998 | Musgrave et al. |
| 5,813,411 A | 9/1998 | Van Bladel et al. |
| 5,817,069 A | 10/1998 | Arnett |
| 5,827,202 A | 10/1998 | Miraki et al. |
| 5,839,470 A | 11/1998 | Hiejima et al. |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,879,332 A | 3/1999 | Schwemberger et al. |
| 5,885,251 A | 3/1999 | Luther |
| 5,891,105 A | 4/1999 | Mahurkar |
| 5,902,274 A | 5/1999 | Yamamoto et al. |
| 5,902,832 A | 5/1999 | Van Bladel et al. |
| 5,913,848 A | 6/1999 | Luther et al. |
| 5,916,208 A | 6/1999 | Luther et al. |
| 5,928,199 A | 7/1999 | Nakagami |
| 5,944,690 A | 8/1999 | Falwell et al. |
| 5,947,930 A | 9/1999 | Schwemberger et al. |
| 5,951,520 A | 9/1999 | Burzynski et al. |
| 5,954,698 A | 9/1999 | Pike |
| 5,957,893 A | 9/1999 | Luther et al. |
| 5,964,744 A | 10/1999 | Balbierz et al. |
| 5,997,510 A | 12/1999 | Schwemberger |
| 6,004,294 A | 12/1999 | Brimhall et al. |
| 6,004,295 A | 12/1999 | Langer et al. |
| 6,011,988 A | 1/2000 | Lynch et al. |
| 6,022,319 A | 2/2000 | Willard et al. |
| 6,045,734 A | 4/2000 | Luther et al. |
| 6,056,726 A | 5/2000 | Isaacson |
| 6,066,100 A | 5/2000 | Willard et al. |
| 6,080,137 A | 6/2000 | Pike |
| 6,126,641 A | 10/2000 | Shields |
| 6,139,532 A | 10/2000 | Howell et al. |
| 6,176,842 B1 | 1/2001 | Tachibana et al. |
| 6,203,527 B1 | 3/2001 | Zadini et al. |
| 6,213,978 B1 | 4/2001 | Voyten |
| 6,228,062 B1 | 5/2001 | Howell et al. |
| 6,228,073 B1 | 5/2001 | Noone et al. |
| 6,268,399 B1 | 7/2001 | Hultine et al. |
| 6,270,480 B1 | 8/2001 | Dorr et al. |
| 6,309,379 B1 | 10/2001 | Willard et al. |
| 6,368,337 B1 | 4/2002 | Kieturakis et al. |
| 6,379,333 B1 | 4/2002 | Brimhall et al. |
| D457,955 S | 5/2002 | Bilitz |

(56) References Cited

U.S. PATENT DOCUMENTS

| | | |
|---|---|---|
| D460,179 S | 7/2002 | Isoda et al. |
| 6,422,989 B1 | 7/2002 | Hektner |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,497,681 B1 | 12/2002 | Brenner |
| D471,980 S | 3/2003 | Caizza |
| 6,527,759 B1 | 3/2003 | Tachibana et al. |
| 6,540,725 B1 | 4/2003 | Ponzi |
| 6,544,239 B2 | 4/2003 | Kinsey et al. |
| 6,547,762 B1 | 4/2003 | Botich et al. |
| 6,582,402 B1 | 6/2003 | Erskine |
| 6,595,955 B2 | 7/2003 | Ferguson et al. |
| 6,626,869 B1 | 9/2003 | Bint |
| 6,632,201 B1 | 10/2003 | Mathias et al. |
| 6,638,252 B2 | 10/2003 | Moulton et al. |
| 6,645,178 B1 | 11/2003 | Junker et al. |
| 6,652,490 B2 | 11/2003 | Howell |
| 6,663,592 B2 | 12/2003 | Rhad et al. |
| 6,666,865 B2 | 12/2003 | Platt |
| 6,679,900 B2 | 1/2004 | Kieturakis et al. |
| 6,695,856 B2 | 2/2004 | Kieturakis et al. |
| 6,695,860 B1 | 2/2004 | Ward et al. |
| 6,712,790 B1 | 3/2004 | Prestidge et al. |
| 6,749,588 B1 | 6/2004 | Howell et al. |
| 6,796,962 B2 | 9/2004 | Ferguson et al. |
| 6,860,871 B2 | 3/2005 | Kuracina et al. |
| 6,902,546 B2 | 6/2005 | Ferguson |
| 6,916,311 B2 | 7/2005 | Vojtasek |
| 6,953,448 B2 | 10/2005 | Moulton et al. |
| 6,960,191 B2 | 11/2005 | Howlett et al. |
| 6,972,002 B2 | 12/2005 | Thorne |
| 7,001,396 B2 | 2/2006 | Glazier et al. |
| 7,004,927 B2 | 2/2006 | Ferguson et al. |
| 7,025,746 B2 | 4/2006 | Tal |
| 7,141,040 B2 | 11/2006 | Lichtenberg |
| 7,153,276 B2 | 12/2006 | Barker et al. |
| 7,179,244 B2 | 2/2007 | Smith et al. |
| 7,191,900 B2 | 3/2007 | Opie et al. |
| 7,303,548 B2 | 12/2007 | Rhad et al. |
| 7,354,422 B2 | 4/2008 | Riesenberger et al. |
| 7,422,572 B2 | 9/2008 | Popov et al. |
| 7,458,954 B2 | 12/2008 | Ferguson et al. |
| 7,494,010 B2 | 2/2009 | Opie et al. |
| 7,530,965 B2 | 5/2009 | Villa et al. |
| 7,566,323 B2 | 7/2009 | Chang |
| D601,243 S | 9/2009 | Bierman et al. |
| 7,611,485 B2 | 11/2009 | Ferguson |
| 7,618,395 B2 | 11/2009 | Ferguson |
| 7,654,988 B2 | 2/2010 | Moulton et al. |
| 7,658,725 B2 | 2/2010 | Bialecki et al. |
| D612,043 S | 3/2010 | Young et al. |
| D615,197 S | 5/2010 | Koh et al. |
| 7,722,567 B2 | 5/2010 | Tal |
| D617,893 S | 6/2010 | Bierman et al. |
| 7,736,339 B2 | 6/2010 | Woehr et al. |
| 7,753,887 B2 | 7/2010 | Botich et al. |
| 7,762,993 B2 | 7/2010 | Perez |
| 7,798,994 B2 | 9/2010 | Brimhall |
| 7,828,773 B2 | 11/2010 | Swisher et al. |
| 7,905,857 B2 | 3/2011 | Swisher |
| 7,922,696 B2 | 4/2011 | Tal et al. |
| 7,922,698 B2 | 4/2011 | Riesenberger et al. |
| 7,935,080 B2 | 5/2011 | Howell et al. |
| 8,029,472 B2 | 10/2011 | Leinsing et al. |
| D653,329 S | 1/2012 | Lee-Sepsick |
| D667,111 S | 9/2012 | Robinson |
| 8,273,054 B2 | 9/2012 | St. Germain et al. |
| D672,456 S | 12/2012 | Lee-Sepsick |
| 8,337,471 B2 | 12/2012 | Baid |
| 8,932,258 B2 | 1/2015 | Blanchard et al. |
| 2003/0032922 A1 | 2/2003 | Moorehead |
| 2003/0153874 A1 | 8/2003 | Tal |
| 2003/0187396 A1 | 10/2003 | Ponzi |
| 2004/0092879 A1 | 5/2004 | Kraus et al. |
| 2004/0111059 A1 | 6/2004 | Howlett et al. |
| 2004/0236288 A1 | 11/2004 | Howell et al. |
| 2005/0020940 A1 | 1/2005 | Opie et al. |
| 2005/0040061 A1 | 2/2005 | Opie et al. |
| 2005/0197623 A1 | 9/2005 | Leeflang et al. |
| 2005/0245847 A1 | 11/2005 | Schaeffer |
| 2005/0273057 A1 | 12/2005 | Popov |
| 2006/0229563 A1* | 10/2006 | O'Reagan et al. ....... 604/164.08 |
| 2007/0060999 A1 | 3/2007 | Randall et al. |
| 2007/0100284 A1 | 5/2007 | Leinsing et al. |
| 2007/0191777 A1 | 8/2007 | King |
| 2007/0193903 A1 | 8/2007 | Opie et al. |
| 2008/0108944 A1 | 5/2008 | Woehr et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2010/0036331 A1 | 2/2010 | Sen |
| 2010/0094310 A1 | 4/2010 | Warring et al. |
| 2010/0168674 A1 | 7/2010 | Shaw et al. |
| 2010/0204675 A1 | 8/2010 | Woehr et al. |
| 2010/0210934 A1 | 8/2010 | Belson |
| 2010/0246707 A1 | 9/2010 | Michelitsch |
| 2010/0331732 A1 | 12/2010 | Raulerson et al. |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0137252 A1 | 6/2011 | Oster et al. |
| 2011/0251559 A1 | 10/2011 | Tal et al. |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2012/0078231 A1 | 3/2012 | Hoshinouchi |
| 2012/0123332 A1 | 5/2012 | Erskine |
| 2012/0184896 A1 | 7/2012 | DeLegge et al. |
| 2012/0220956 A1 | 8/2012 | Kuracina et al. |
| 2014/0031752 A1 | 1/2014 | Blanchard et al. |
| 2014/0094774 A1 | 4/2014 | Blanchard |

FOREIGN PATENT DOCUMENTS

| | | | |
|---|---|---|---|
| EP | 2569046 A1 | 3/2013 | |
| JP | 2013-529111 | 7/2013 | |
| WO | 0012167 A1 | 3/2000 | |
| WO | 0107103 A1 | 2/2001 | |
| WO | 0241932 A2 | 5/2002 | |
| WO | 2004106203 A2 | 12/2004 | |
| WO | 2005002659 A1 | 1/2005 | |
| WO | 2008030999 A2 | 3/2008 | |
| WO | 2009031161 A1 | 3/2009 | |
| WO | WO 2009/114837 A2 * | 9/2009 | ............ A61M 25/06 |
| WO | 2010015676 A1 | 2/2010 | |
| WO | 2011036574 A1 | 3/2011 | |
| WO | 2011143621 A1 | 11/2011 | |
| WO | 2012154277 A1 | 11/2012 | |
| WO | 2014133617 A1 | 9/2014 | |

OTHER PUBLICATIONS

Access Scientific, The Powerwand® Extended Dwell Catheter Brochure.

BD Angiocath ™ Autoguard™ Shielded IV Catheter Brochure, © 2001.

BD Medical Systems, I.V. Catheter Family Brochure.

BD Saf-T-Intiman ™ Integrated Safety IV Catheter Brochure, © 2001.

Becton Dickinson, Insyte® AutoGuard™ Shielded I.V. Catheter Brochure, 1998.

Hadaway, Lynn C., A Midline Alternative to Central and Peripheral Venous Access, Caring Magazine, May 1990, pp. 45-50.

Menlo Care, Landmarkm™ Aquavene® Catheters Brochure, 1992.

Menlo Care, Landmark® Midline Catheter Maintenance and Reference Guide.

(56) References Cited

OTHER PUBLICATIONS

Menlo Care, Landmark® Midline Catheters Brochure, 1991.
Menlo Care, Landmark® Venous Access Device Insertion Instructions.
Menlo Care, Publications on Aquavene® Technology, Aug. 1992.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Search Report and Written Opinion dated Jun. 25, 2012.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
CN 201180029526.7 filed Dec. 14, 2012 First Office Action dated Apr. 21, 2014.
PCT/US2012/026618 International Preliminary Report on Patentability dated Aug. 27, 2013.
PCT/US2013/073577 filed Dec. 6, 2013 International Search Report and Written Opinion dated Feb. 24, 2014.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 14/044,623, filed Oct. 2, 2013 Notice of Allowance dated Nov. 6, 2014.

* cited by examiner

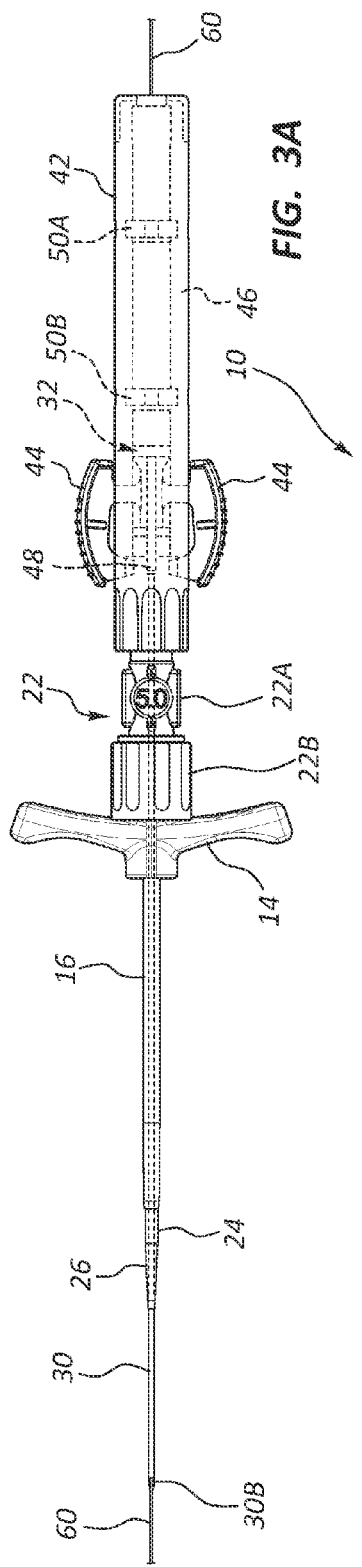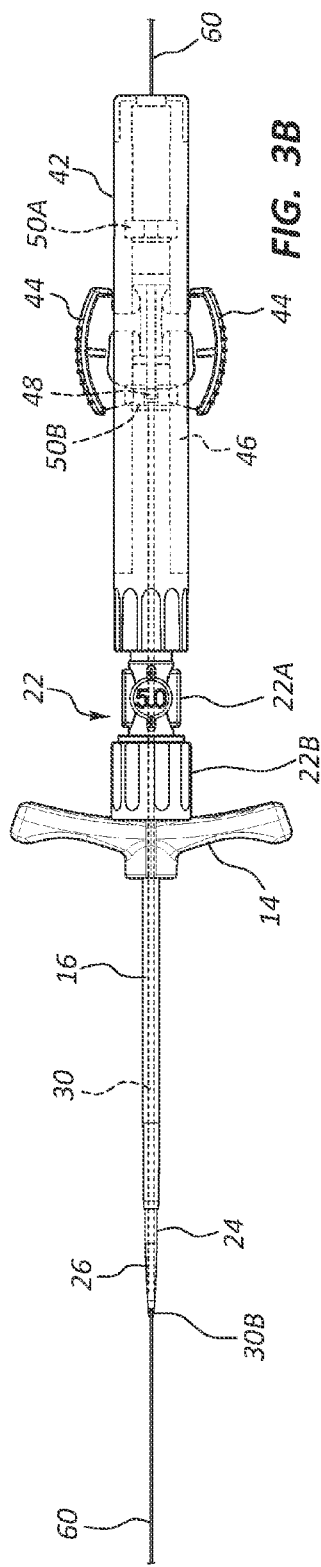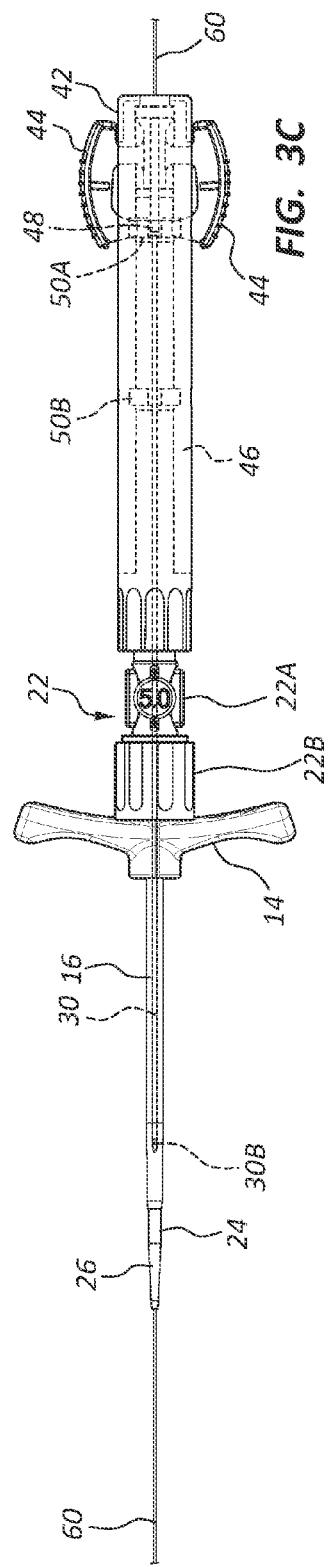

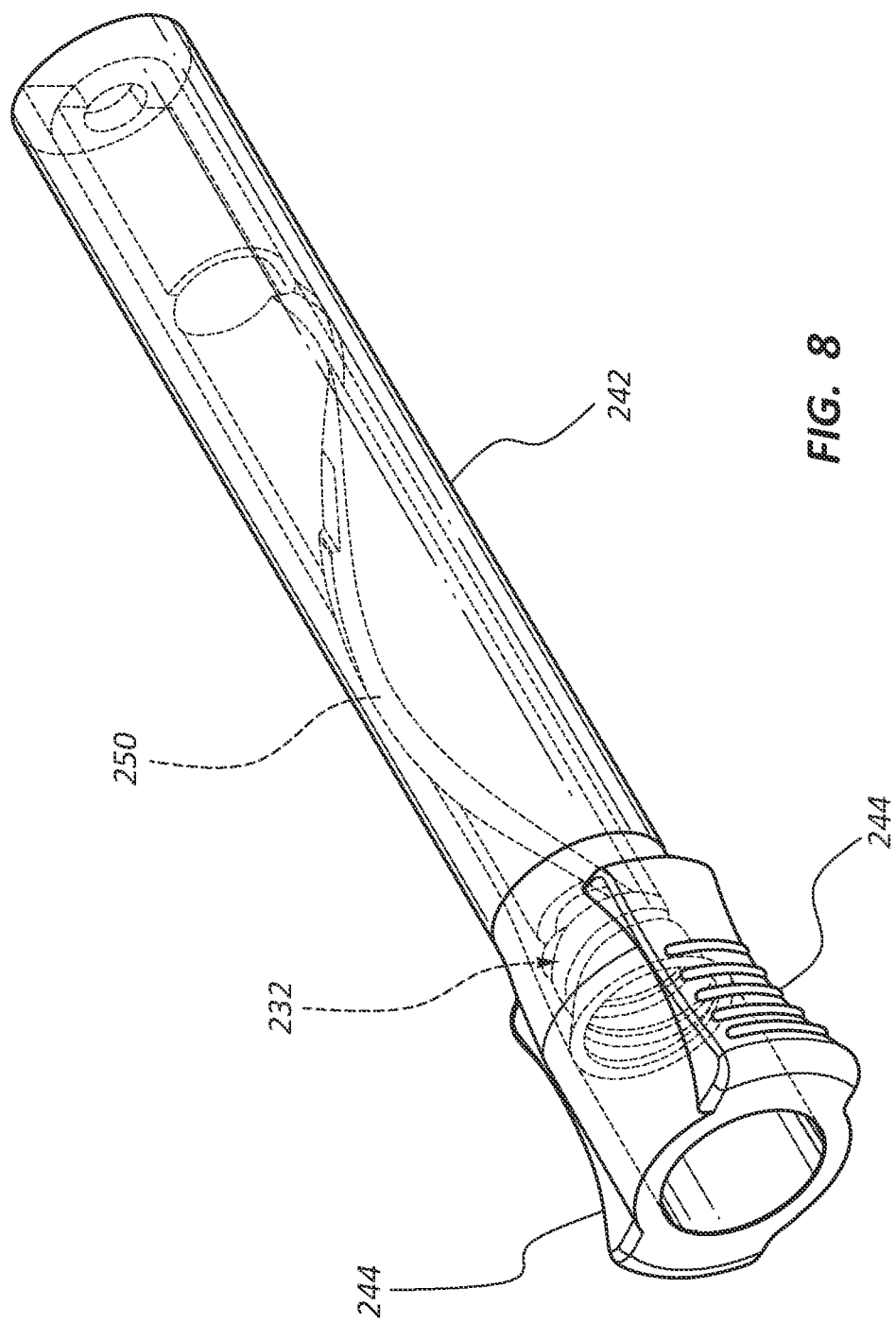

MEDICAL COMPONENT INSERTION DEVICE INCLUDING A RETRACTABLE NEEDLE

CROSS-REFERENCE TO RELATED APPLICATIONS

This application claims the benefit of U.S. Provisional Patent Application No. 61/446,817, filed Feb. 25, 2011, and titled "Introducer Assembly Including a Retractable Needle," which is incorporated herein by reference in its entirety.

BRIEF SUMMARY

Briefly summarized, embodiments of the present invention are directed to an insertion device for use in assisting with the placement of a medical device within the body of a patient. For example, the insertion device can be employed to assist with the placement of an introducer, which provides a conduit into the body to enable insertion of a catheter.

In one embodiment, the insertion device comprises a needle that is removably disposed within a bore defined by the medical device, and a needle retraction assembly. The needle retraction assembly is capable of positioning the needle in any one of a first position wherein a distal tip of the needle is disposed a predetermined distance distal to a distal end of the medical device, a second position wherein the needle distal tip is disposed distal but proximate to the distal end of the medical device, and a third position wherein the needle distal tip is retracted within the medical device bore.

As mentioned, in one embodiment the medical device is an introducer assembly that includes a dilator coaxially disposed within a sheath, with the needle disposed within a bore defined by the dilator. The needle retraction assembly can include a housing that is releasably attached to a proximal end of the dilator. A hub of the needle can be slidably disposed within the housing the enable manual movement of the needle between any of the three needle positions described above. As will be seen, each of the three needle positions facilitates simple insertion of the medical device into the patient while minimizing trauma thereto.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 3A-3C show the insertion device of FIGS. 1A-1C in various configurations;

FIG. 8 shows a housing of an insertion device according to one embodiment; and

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to an insertion device for use in assisting with the placement of a medical device within the body of a patient. For example, the insertion device can be employed to assist with the placement of an introducer, which provides a conduit into the body of the patient to enable insertion of a catheter therethrough. In another example, the insertion device can be used to place a catheter directly into the patient's body without the use of an introducer. Other medical devices can also be placed with the insertion device described herein. In one embodiment, the insertion device includes a needle that is positionable in one of three or more positions during use of the device so as to ease insertion of the medical device into the body.

Figure 1A:
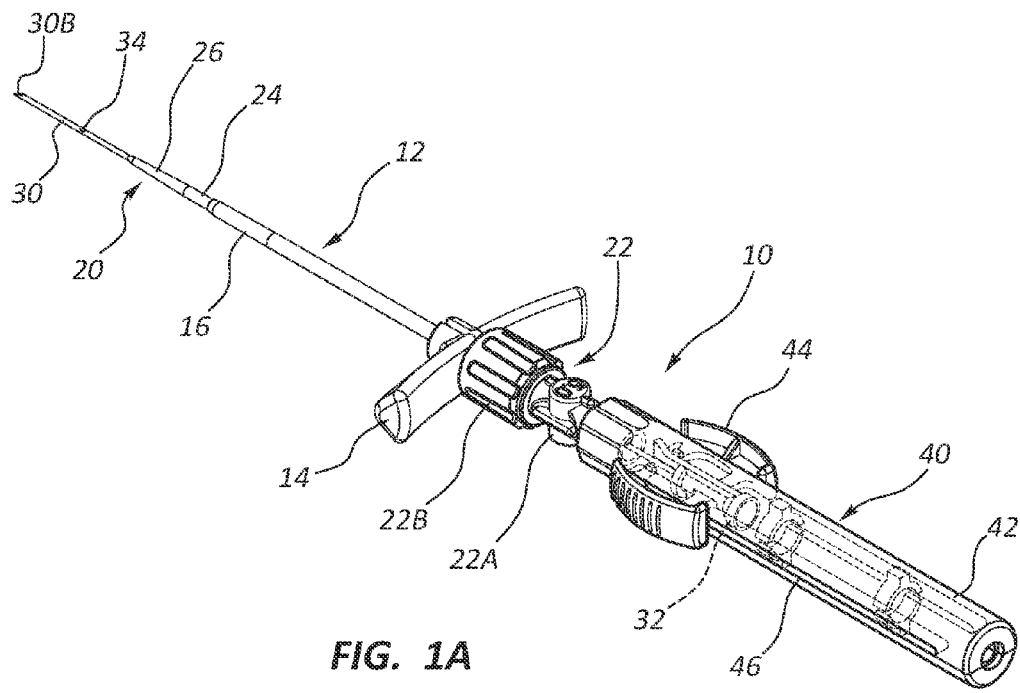
FIGS. 1A-1C are various views of an insertion device according to one embodiment.
Figure 1B:
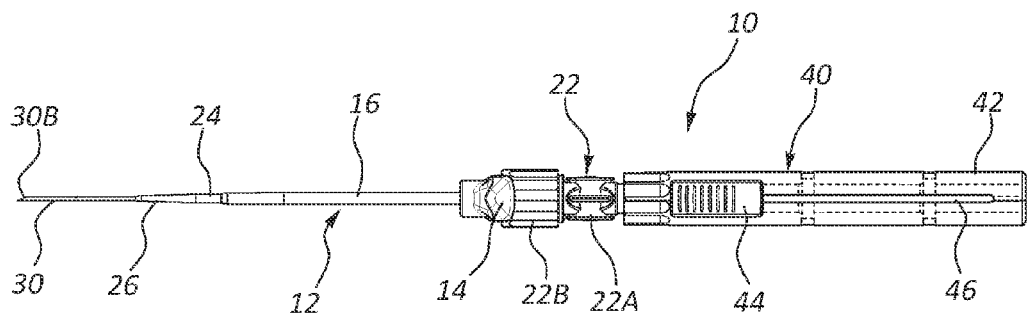
Figure 1C:
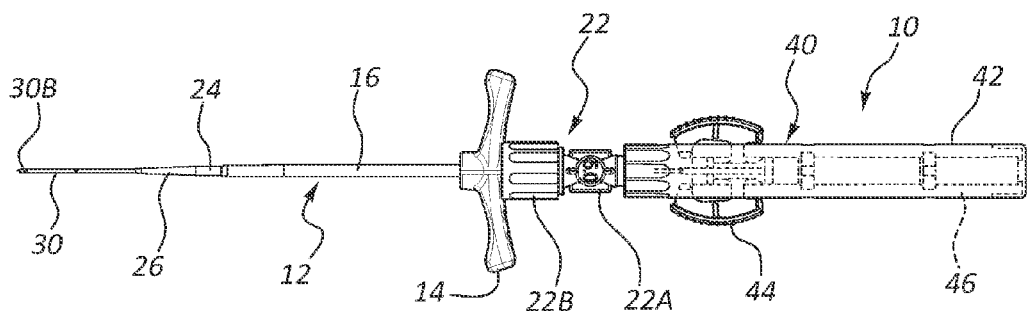

Reference is first made to FIGS. 1A-1C, which show various details regarding an insertion device, generally designated at 10, according to one embodiment. As shown, the device 10 is initially mated with an introducer 12, which in turn includes an introducer hub 14 and a sheath body ("sheath") 16 extending distal from the hub. The introducer hub 14 defines a handle for use in manipulating the introducer 12 during use. The introducer hub 14 and the sheath 16 of the introducer 12 together define a longitudinal bore. Though configured to be splittable here, the introducer in other embodiments need not be splittable.

A dilator 20 is coaxially disposed within the bore of the introducer 12. As shown, the dilator 20 includes a hub 22 and a body 24 extending distally from the hub. The dilator hub 22 and body 24 together define a bore therethrough for the passage of an optional guidewire. The dilator hub 22 defines a base portion 22A and a cap portion 22B. The cap portion 22B is configured to threadably engage the hub 14 of the introducer 12 so as to releasably mate the introducer and the dilator 20 as shown in FIGS. 1A-1C. In this mated configuration, it is seen that a tapered distal portion 26 of the dilator body 24 extends beyond the distal end of the introducer sheath 16.

Figure 2A:
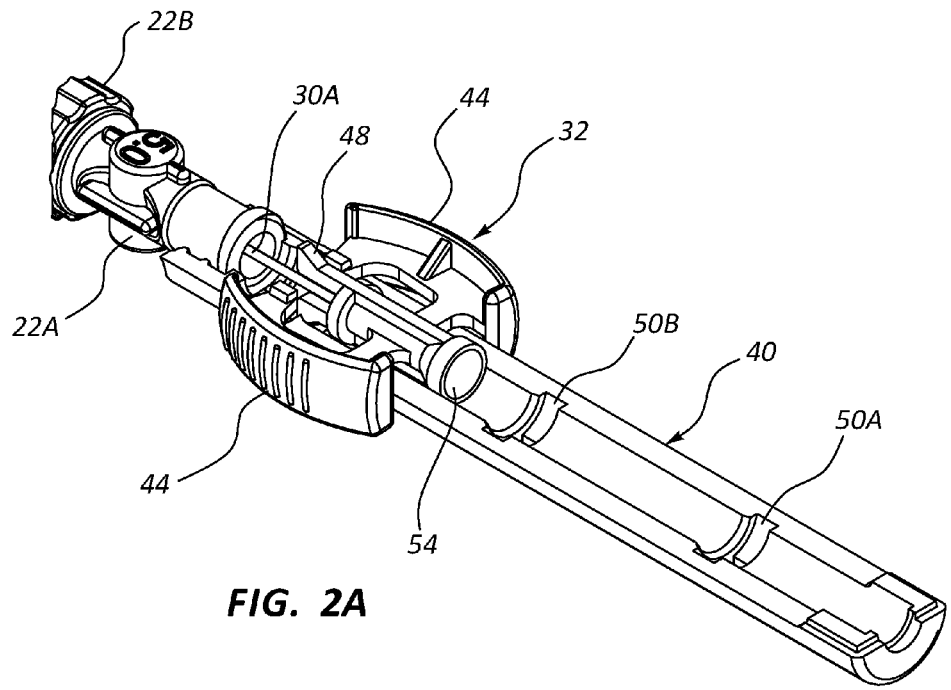
FIGS. 2A and 2B are partial cutaway views of the insertion device of FIGS. 1A-1C.
Figure 2B:
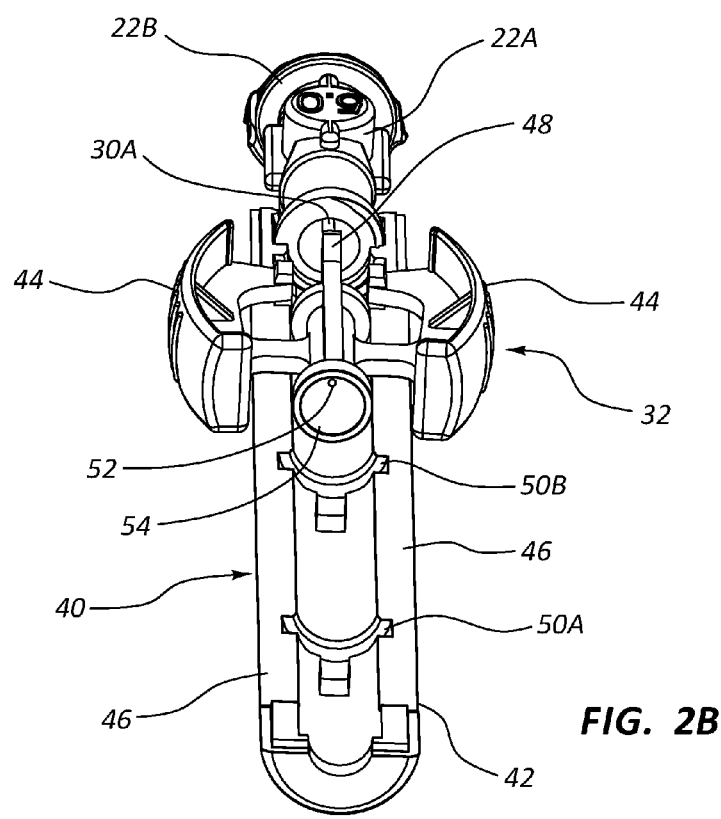

FIGS. 1A-1C further show a hollow needle 30 coaxially disposed within the bore of the dilator 20 such that a sharpened distal tip 30B thereof initially extends distally past the tapered portion 26 of the dilator 20. A proximal end 30A of the needle 30 is connected to a needle hub 32 (FIGS. 2A, 2B). The needle hub 32 cooperates with a needle retraction assembly 40 to selectively move the needle 30 axially with respect the introducer assembly, as will be described. A flash hole 34 can be included in the wall of the needle 30 near the distal tip 30B thereof in order to help detect the presence of blood and confirm positioning of the needle distal tip within a vein, for instance. The flash hole or other suitable component for confirming the presence of blood in the needle in other embodiments may be placed in other locations on the device. In one embodiment, for instance, a flash window can be provided in or near the dilator hub base 22A. Also, though hollow here, in other embodiments the needle may be solid.

A needle retraction assembly 40 is included with the insertion device 10 and includes a housing 42 that threadably engages with the base portion 22A of the dilator hub 22. The housing 42 defines a cavity in which is slidably disposed the hub 32 of the needle 30. The needle 30 extends distally from the needle hub 32 through the bore defined by the hub 22 and body 24 of the dilator 20 to extend beyond the tapered distal portion 26 of the dilator, as shown.

Two handles 44 of the needle hub 32 extend exteriorly to the needle retraction housing 42 via a longitudinally extending slot 46 defined in the housing 42. Thus, sliding movement of the needle hub 32 within the housing 42 toward the proximal end thereof causes corresponding proximal movement of the distal tip 30B of the needle 30. Likewise, distal movement of the needle hub 32 within the housing 42 toward the distal end thereof causes corresponding distal movement of the needle distal tip 30B. It is thus seen that the handles 44 provide one way of selectively moving the needle hub 32 and needle 30. It should be appreciated, however, that other structures or methods may be used to selectively move the needle, including springs or other biasing elements, automatic or machine or electronic-based actuators, etc. Also, though present in the illustrated embodiment, it is appreciated that in other embodiments no housing is included with the needle retraction assembly.

FIGS. 2A and 2B depict further details regarding the needle hub 32 and needle retraction assembly 40. A needle hub position locking feature is included with the needle hub 32, here implemented as two opposing teeth 48 radially extending from the needle hub. The teeth 48 are configured to engage notches 50 included with the housing 42 when the needle hub 32 is axially slid within the housing, thus locking the needle hub at predetermined locations within the needle retraction assembly housing 40. In particular, a proximal notch 50A and a distal notch 50B are included in the housing 42 and will be described further below.

As best seen in FIG. 2B, the needle hub 32 further defines a conduit 52 coaxial with the hollow needle 30 so as to be able to pass a guidewire, such as the guidewire 60 shown in FIG. 3A, through the housing 42, needle hub, and needle of the insertion device 10 such that the guidewire extends past the distal tip 30B of the needle. A conical structure 54 is defined at the proximal end of the conduit 52 to ease insertion of the guidewire 60 into the needle hub 32. In another embodiment, no guidewire is included with the insertion device, and no guidewire conduits are provided.

In accordance with the present embodiment, the needle 30 of the insertion device 10 is axially movable with respect to the introducer assembly As mentioned above, the needle retraction assembly 40 includes structure to enable the needle to be selectively moved in order to facilitate ease of insertion of a medical device in which the insertion device 10 is disposed, in this case an introducer assembly (FIGS. 1A-1C). Note that though an introducer assembly is shown here, in other embodiments a variety of medical devices can be inserted into a patient with the assistance of the insertion device described herein, as illustrated further below.

In particular, FIG. 3A shows a first position of the needle 30 with respect to the sheath 12 and dilator 20 of the introducer assembly, wherein the distal tip 30B of the needle extends distally beyond the distal end of the dilator body 24 a predetermined distance. This extension of the needle distal tip 30B corresponds to the position of the needle hub 32 proximate the distal end of the housing 42 of the needle retraction assembly 40, as seen in FIGS. 2A and 2B. This position of the distal tip 32B of the needle 30 is also referred to herein as position 1. In position 1, the needle 30 is positioned to gain access to an internal portion of the body of the patient, such as a vein or other vessel. The guidewire 60 is also shown slidably disposed within, and extending through, the needle retraction assembly 40 and the introducer assembly so as to extend distally from the needle distal tip 32B.

Note that the particular distance of needle distal tip extension past the dilator distal end in other embodiments can vary according to various factors, including needle length, distance of needle hub travel within the needle retraction assembly housing, length of the medical device, etc.

FIG. 3B shows a second position of the needle 30 with respect to the sheath 12 and dilator 20 of the introducer assembly, wherein the distal tip 30B of the needle extends distally beyond the distal end of the dilator body 24 a relatively short distance so as to be proximate to the distal end of the tapered distal portion 26 of the dilator body 24. This position of the needle distal tip 30B is achieved when the needle hub 32 is manually slid via user force on the needle hub handles 44 from the position shown in FIG. 3A to the position shown in FIG. 3B, wherein the needle hub is located about mid-way along the length of the needle retraction assembly housing 42. In this position, the teeth 48 of the needle hub 32 frictionally engage the notch 50B, thus locking the needle hub in place until sufficient user force on the handles 44 dislodges it from its location.

The position of the distal tip 32B of the needle 30 in FIG. 3B is also referred to herein as position 2. In position 2, the distal tip 30B of the needle 30 is positioned to assist the tapered distal portion 26 of the dilator body 24 in gaining access to the vessel or other internal body portion of the patient, as will be seen.

FIG. 3C shows a third position of the needle 30 with respect to the sheath 12 and dilator 20 of the introducer assembly, wherein the distal tip 30B of the needle is retracted within the bore of the dilator body 24 so as to be shielded from contact by the dilator body and the body 16 of the introducer 12. This position of the needle distal tip 30B is achieved when the needle hub 32 is manually slid via user force on the needle hub handles 44 from the substantially mid-line position shown in FIG. 3B to the position shown in FIG. 3C, wherein the needle hub is located about proximate the proximal end of the needle retraction assembly housing 42. In this position, the teeth 48 of the needle hub 32 frictionally engage the proximal notch 50A, thus locking the needle hub in place until sufficient user force on the handles 44 dislodges it from its location.

The position of the distal tip 32B of the needle 30 in FIG. 3C is also referred to herein as position 3. In position 3, the distal tip 30B of the needle 30 is retracted and is disposed proximal to the tapered distal portion 26 of the dilator body 24 so as to enable the distal portion of the introducer assembly to flex during advancement into the vessel of the patient, as will be seen. Also, with the needle distal tip 30B safely disposed within the dilator body 24, position 3 prevents the risk of damage to the vessel by the needle 30 while the dilator 20 and introducer 12 are advanced into the vessel. Note further that, though it is described herein as movement of the needle relative to the stationary introducer/dilator, in other embodiments, the introducer and/or dilator can be moved relative to the stationary needle to achieve the three positions described above.

In addition to the teeth and notch locking arrangement described above, it is appreciated that other features for locking the needle hub position with respect to the housing of the needle retraction assembly can be employed as appreciated by one skilled in the art. Also, the number and needle distal tip locations possible with the insertion device can vary from what is described herein. Moreover, the size, shape, and configuration of the insertion device and the medical device it is configured to insert into the body can vary from what is shown and described herein.

Figure 4A:
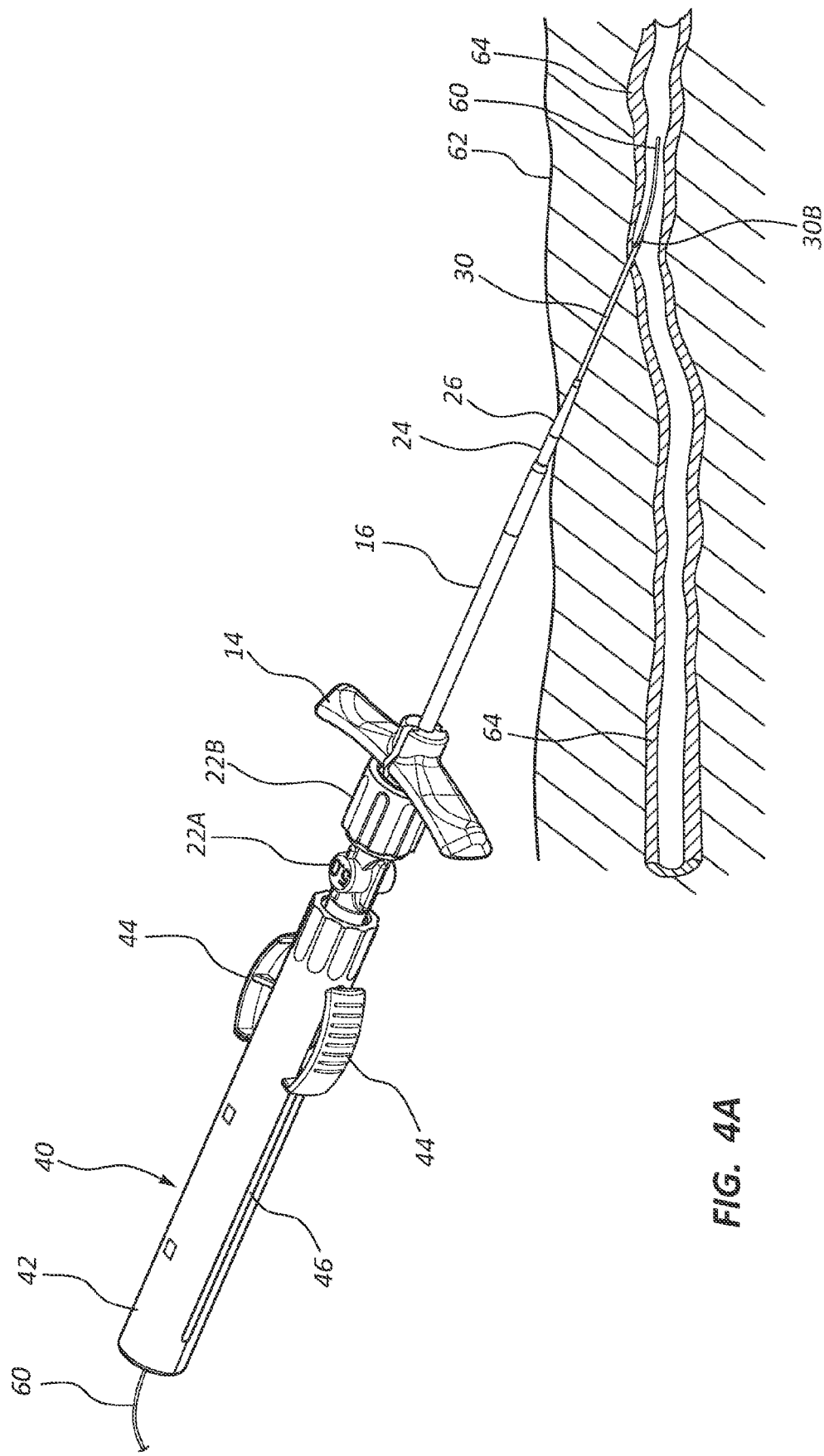
FIGS. 4A-4E show various stages of insertion of an introducer into a patient using an insertion device, according to one embodiment.

FIGS. 4A-4E depict various details regarding the use of the insertion device 10 in assisting with the insertion of an introducer assembly into a vessel of a patient, according to one embodiment. Note that the medical device to be placed and the desired location within the patient body where the device is to be placed can vary from what is described here. In FIG. 4A, the insertion device 10, having been previously attached to the introducer assembly as explained above and with the needle 30 in position 1 (FIG. 3A), the distal tip 30B of the needle is inserted into the skin 62 of the patient and into the lumen of a desired subcutaneous vessel 64. A flash hole 34 (FIG. 1A) defined in the needle 30 can assist in viewing blood return up the needle so as to confirm proper needle placement in the vessel 64, in one embodiment. Once the vessel 64 has been accessed, the guidewire 60 can be manually advanced by the user through the housing 42 of the needle retraction assembly and the needle 30 so as to extend into the vessel lumen.

Figure 4B:
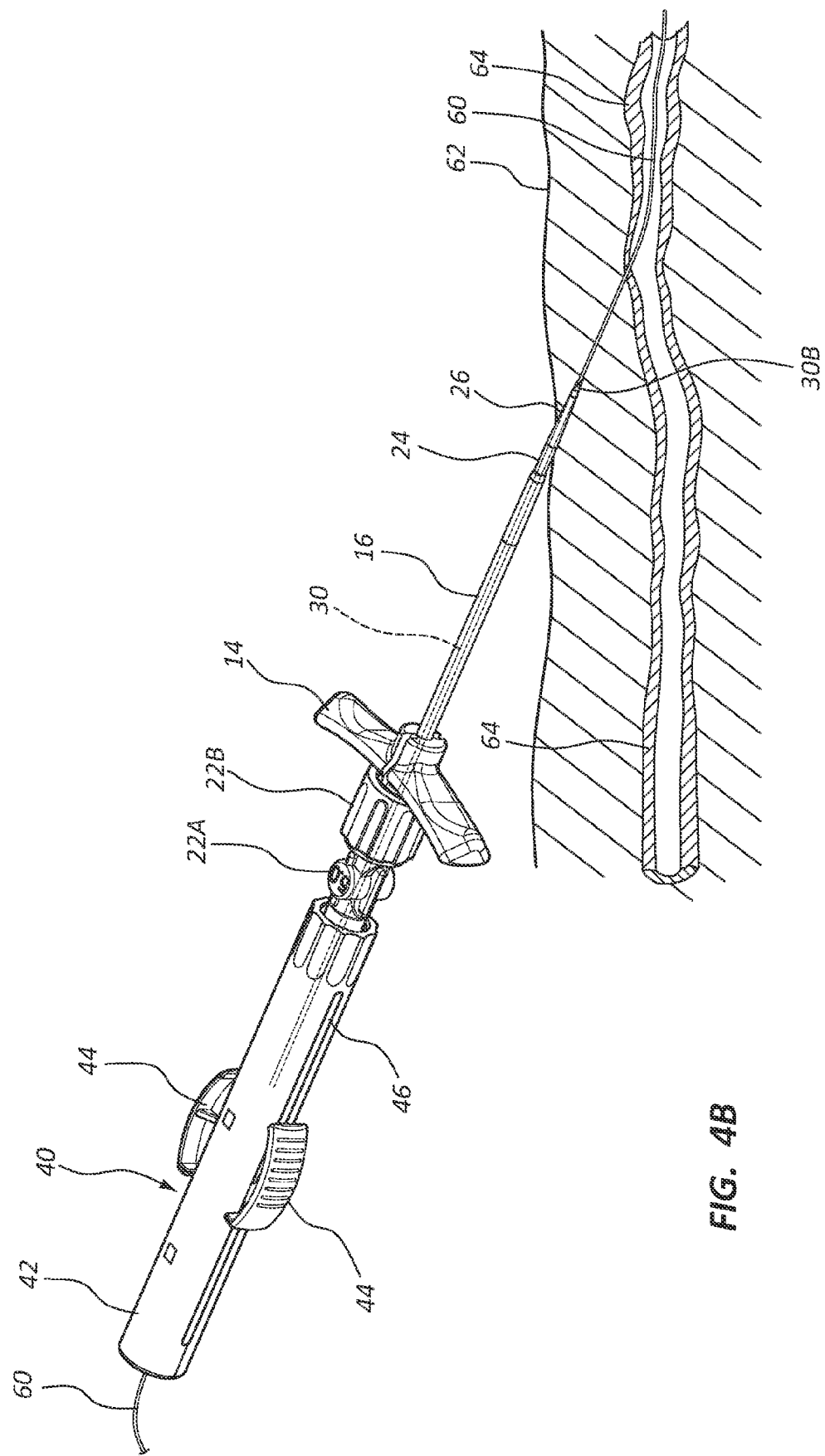
Figure 4C:
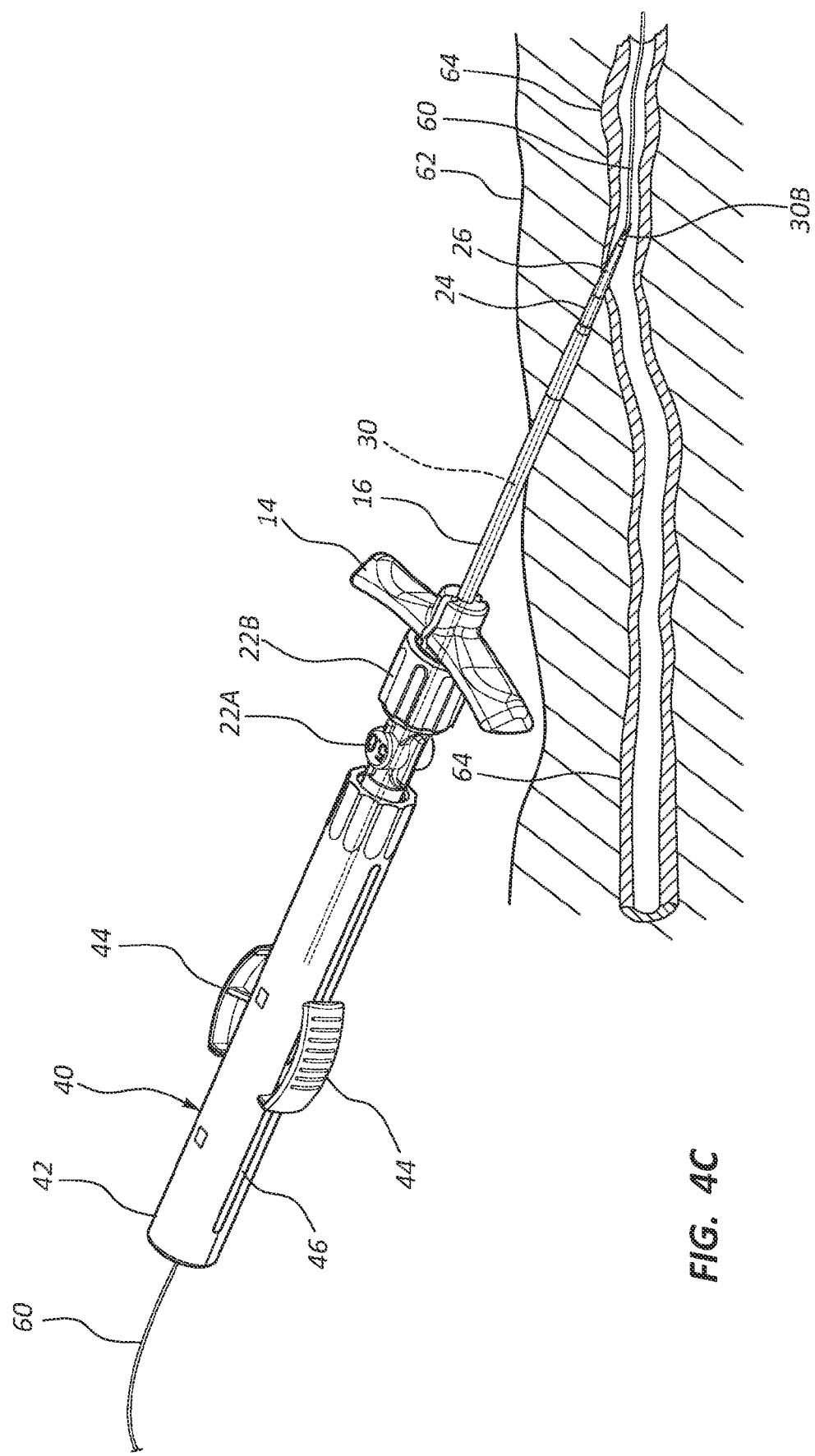

In FIG. 4B, once the guidewire has been inserted into the vessel 64, the needle 30 is retracted to position 2 (FIG. 3B) such that the needle distal tip 30B is proximate the tapered distal portion 26 of the dilator body 24. This may cause the needle distal tip to retract a short distance from the vessel insertion site, as shown, while the guidewire 60 remains in place within the vessel 64 and extending through the vessel insertion site.

Retraction of the needle 30 to position 2 enables the distal tip 30B thereof to assist entry of the tapered distal portion 26 of the dilator body 24 through the vessel insertion site and into the vessel 64 by following the previously placed guidewire 60. It is noted that in one embodiment the needle or another suitable portion of the insertion device or medical component can be treated so as to be ultrasonically visible such that one or more of the stages described herein can be performed with the assistance of ultrasound imaging guidance.

Figure 4D:
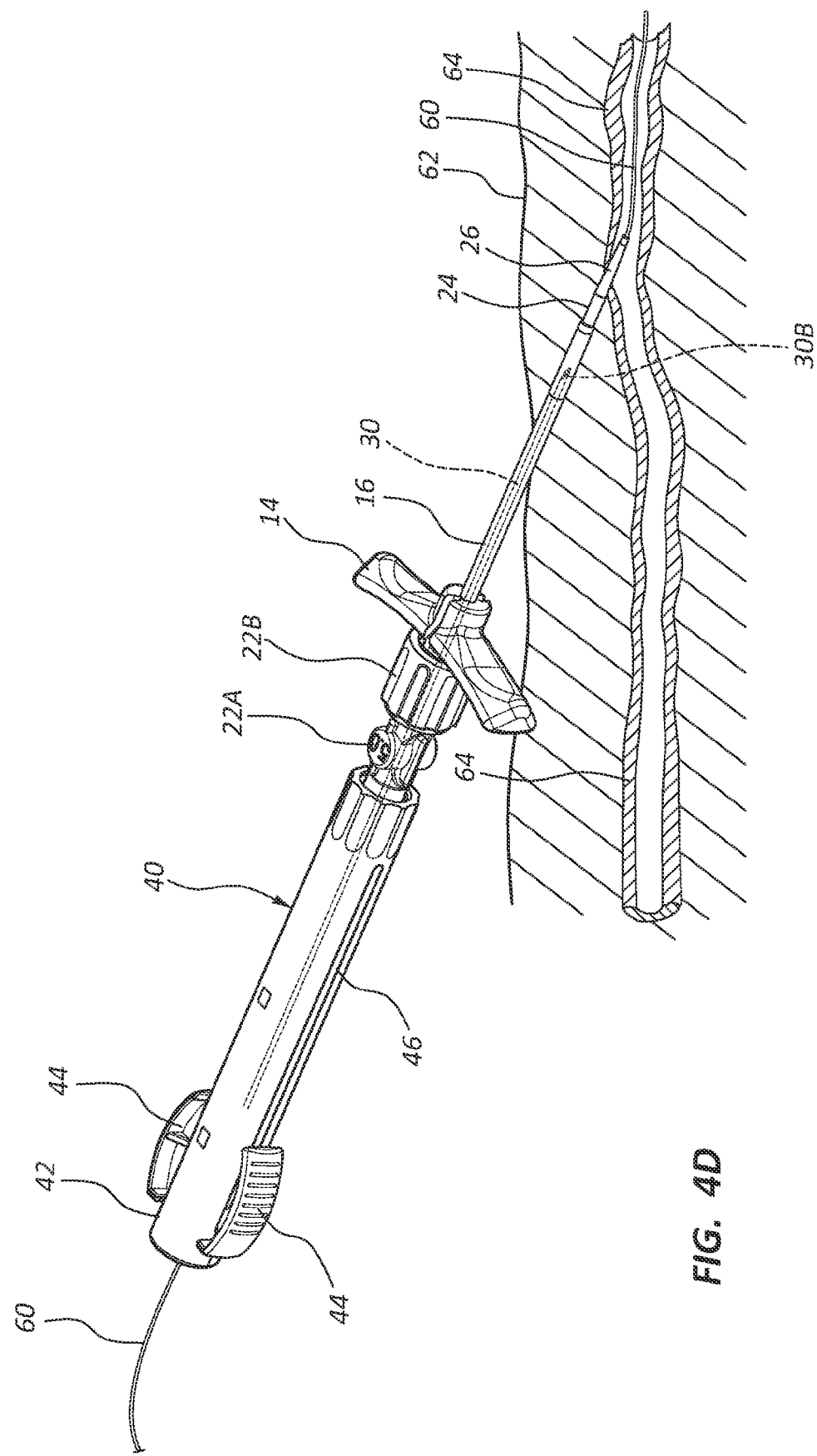

FIG. 4D shows that, once the needle distal tip 30B and tapered distal portion 26 of the dilator body 24 are disposed within the vessel 64, the needle can be retracted to position 3 (FIG. 3C), wherein the distal tip thereof is disposed within the bore of the dilator body 24 a predetermined proximal to the dilator distal end. As has been described, and as is the case with the other needle positions, the needle retraction assembly 40 releasably locks the needle hub 32 in position so the needle distal tip can remain shielded within the dilator bore in position 3. With the needle 30 in position 3, the dilator 20 and introducer 12 can be further advanced distally into the vessel 64 until inserted to the desired extent within the vessel. Because the needle 30 is not present in their distal portions, the introducer 12 and dilator 20 are pliant so as to bend and conform to the shape of the vessel 64.

Figure 4E:
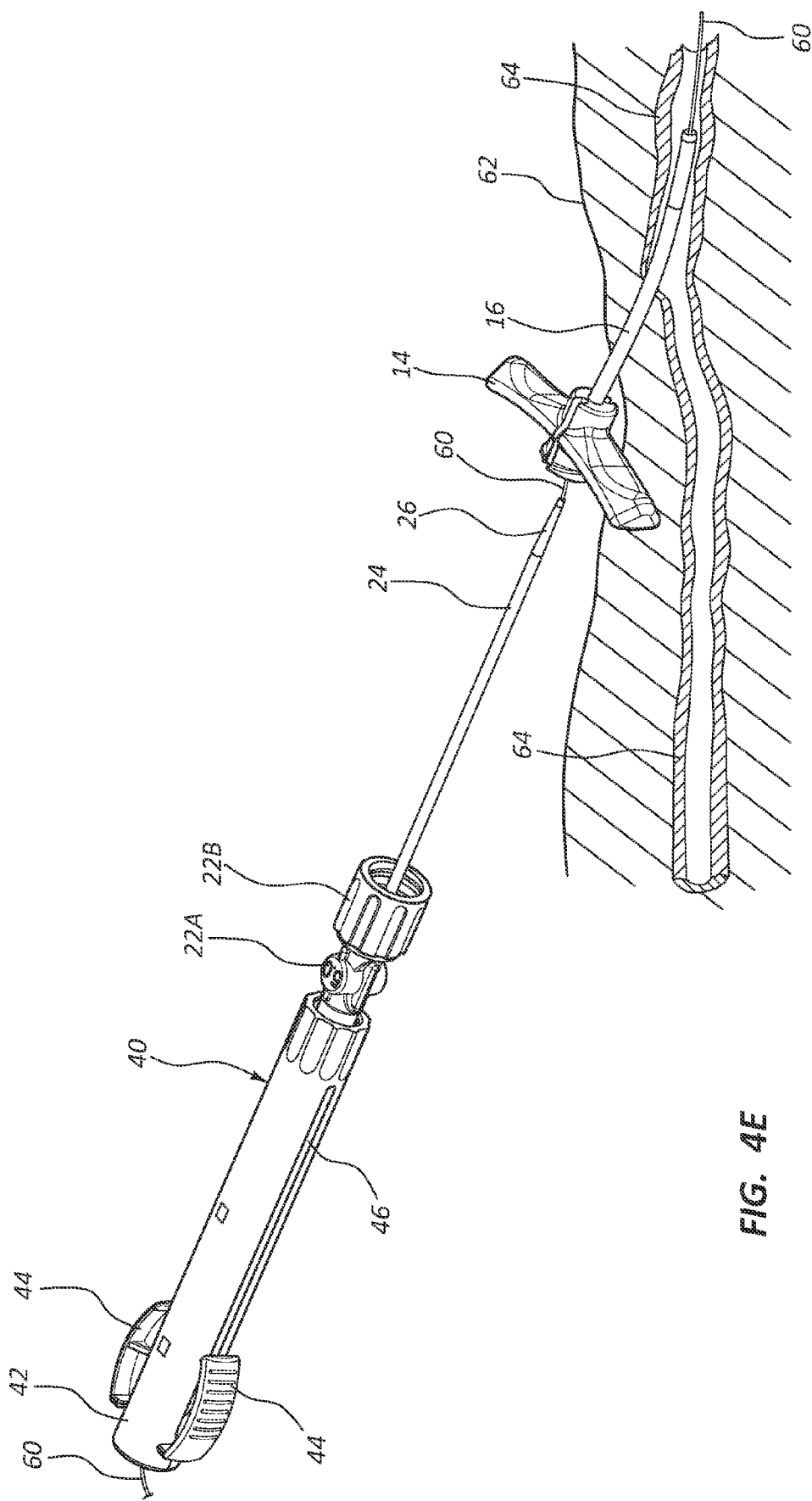

FIG. 4E shows that once the introducer 12 has been inserted a sufficient distance into the vessel 64, the insertion device 10 including the needle 30 and the needle retraction assembly 40, together with the dilator 20, can be removed, thus separating them from the introducer and leaving the introducer disposed within the vessel. A catheter may then be inserted into the vessel 64 through the introducer 12.

If desired, the guidewire 60 can be left in place within the vessel 64 when the insertion device 10 and dilator 20 are removed, as seen in FIG. 4E, to further assist in placement of a catheter or other suitable device through the introducer 12. It is further appreciated that the above method may be performed without the use of a guidewire, in one embodiment.

It is appreciated that catheters of many types, including PICC, PIV, intermediate dwell or mid-line, CVC, and other catheter configurations, can be placed with the present insertion device. Other uses of the insertion device are also contemplated. Non-limiting examples of such other uses include placement of stent grafts, feeding devices, etc. The insertion device is suitable for arterial or venous vessel access, and for use in various body cavities or intracorporeal locations. As mentioned, in the present embodiment the needle 30 is positionable in three positions; however, other possible needle position configurations are also contemplated.

Figure 5A:
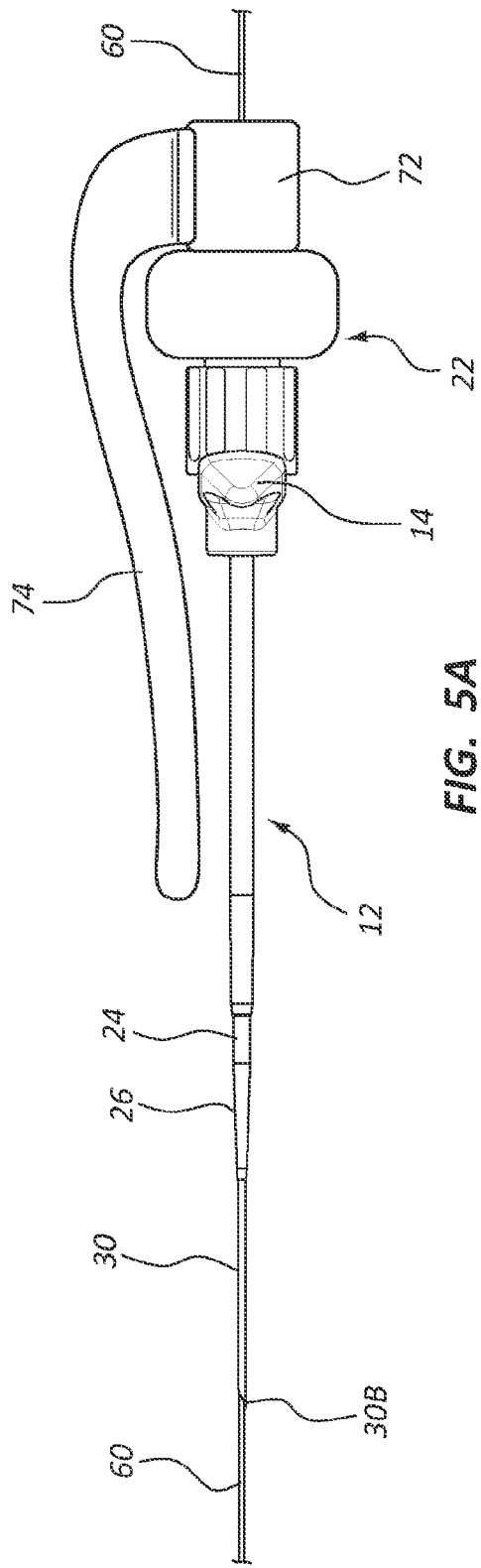
FIGS. 5A and 5B show an insertion device according to one embodiment.
Figure 5B:
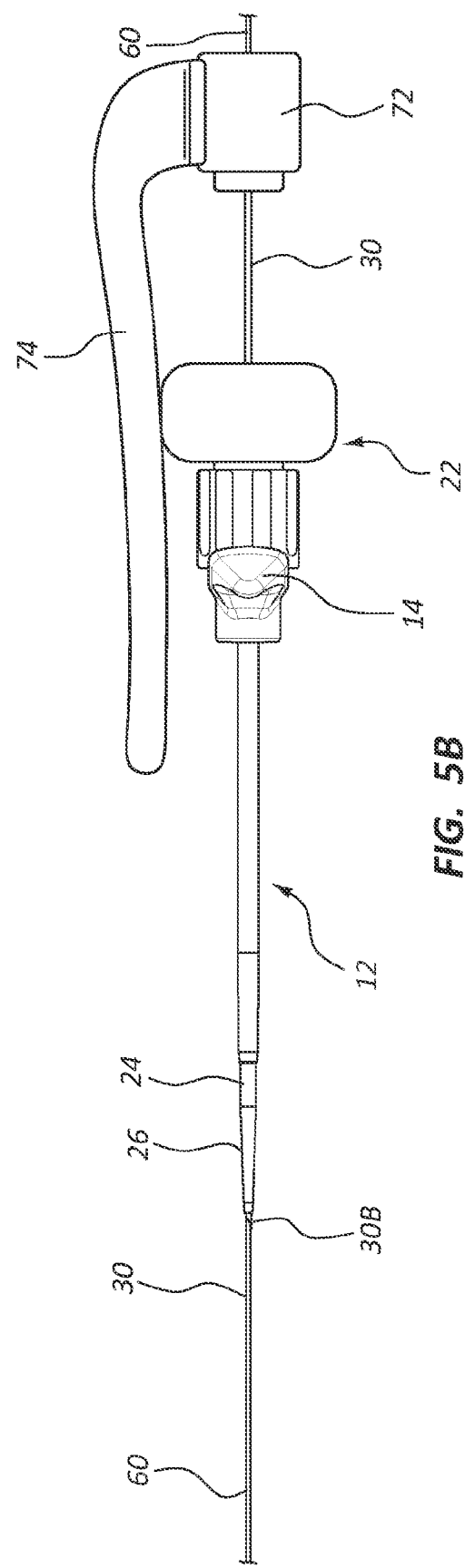

FIGS. 5A and 5B depict the insertion device according to another embodiment, wherein the needle retraction assembly includes no housing. Rather, the needle hub 72 includes a distally extending handle that is shaped and positioned to facilitate one-handed operation of the device, such as retraction of the needle 30, shown in FIG. 5B. These and other variations of the insertion device are therefore contemplated.

Figure 6:
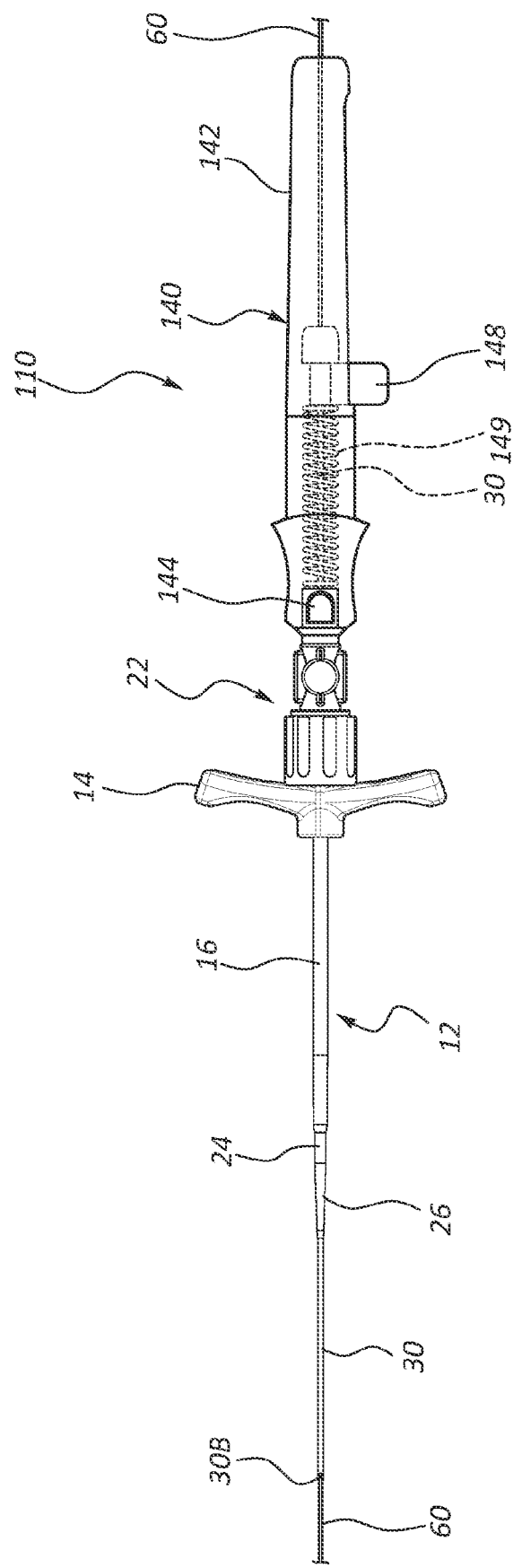
FIG. 6 is a top view of an insertion device according to one embodiment.

FIG. 6 shows details of an insertion device 110 according to one embodiment, wherein a needle retraction assembly 140 includes a housing 142 through at least a portion of which the guidewire 60 extends. A button release 144 is included on the housing 142 for selectively retracting the needle 30 from its position 1, illustrated here, to another position, such as position 2 or position 3 described above. In one embodiment, the button release 144 is operably coupled to a spring 149 or other biasing element disposed within the housing 142 in order to cause retraction of the needle 30. The housing 142 of the needle retraction assembly 140 further includes a handle 148 for selectively advancing the guidewire 60 through the needle 30. Though illustrated in FIG. 6 as extending past the proximal end of the insertion device, the guidewire in another embodiment can be completely contained within the housing of the needle retraction assembly.

Figure 7A:
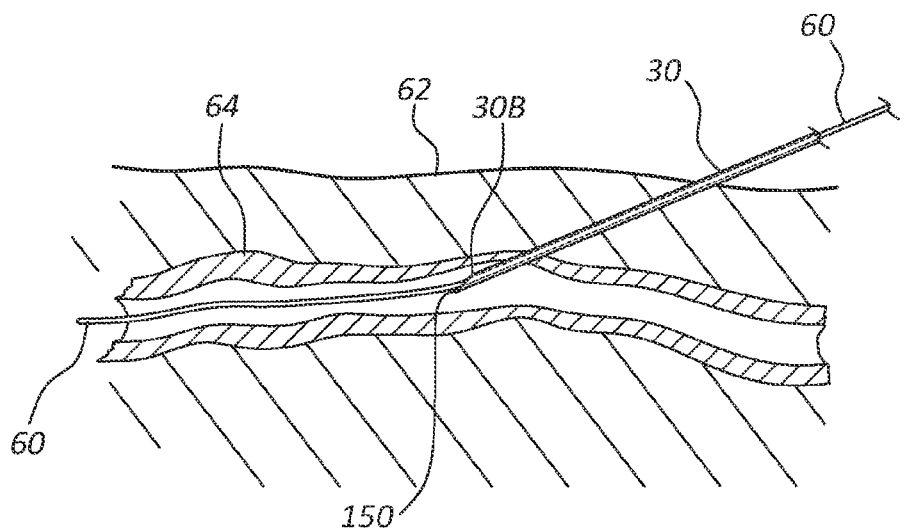
FIGS. 7A-7C show details of insertion of the needle of the insertion device of FIGS. 1A-1C according to one embodiment.
Figure 7B:
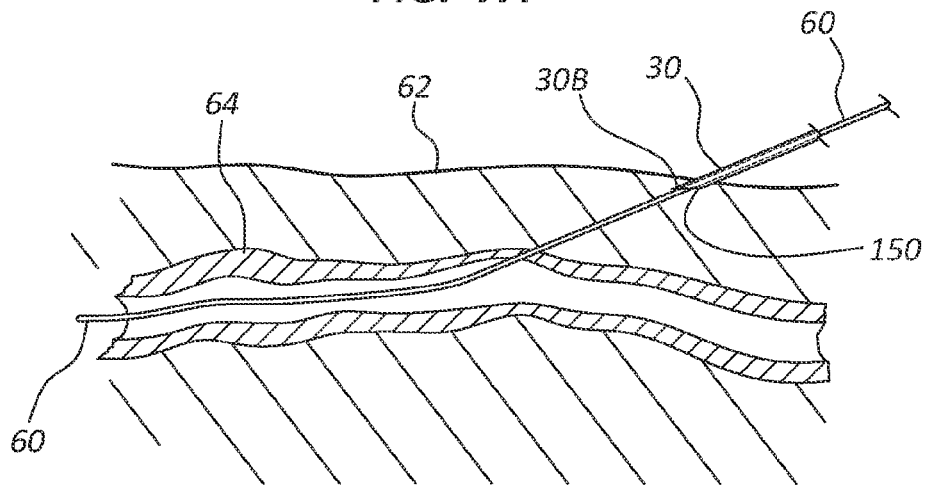
Figure 7C:
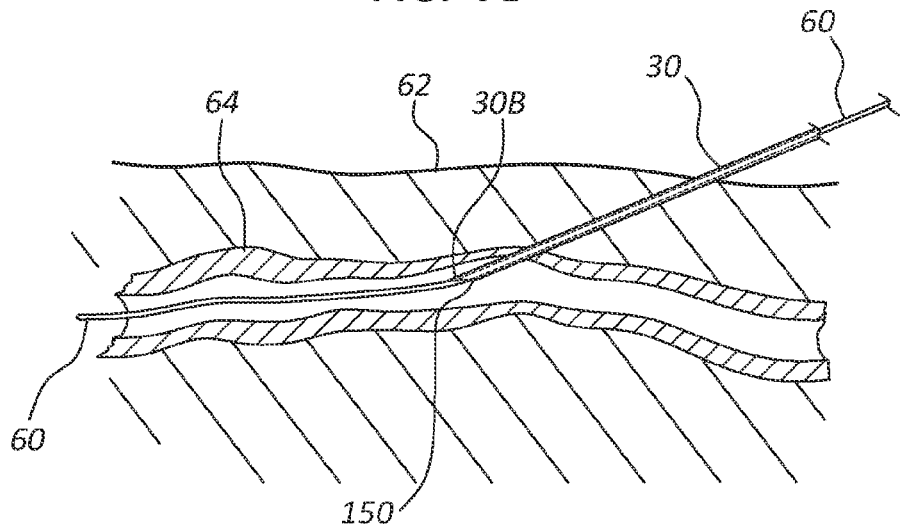

FIGS. 7A-7C illustrate that, in one embodiment, it is desirable to rotate a bevel 150 of the needle 30 from a bevel-up configuration to a bevel-down configuration when moving the needle from position 1 (FIG. 3A) to position 2 (FIG. 3B). In particular, FIG. 7A shows insertion of the needle 30 into the vessel 64 while in position 1, with the bevel 150 of the needle distal tip 30B in an up position, i.e., the angled cutting surface of the needle facing toward the surface of the skin 62. FIG. 7B shows that when the needle 30 is retracted to position 2, the bevel 150 can be rotated to a bevel-down configuration. FIG. 7C shows that the needle 30 can then be reinserted into the vessel 64 while in the bevel-down configuration, as was described in connection with FIGS. 4B and 4C above. This desirably helps to prevent gouging of the vessel 64 caused by inadvertent needle contact with the back wall of the vessel during needle insertion and advancement. In addition, the bevel-down configuration reduces the chance of guidewire severing by the needle distal tip 30B when the needle 30 is advanced into the vessel 64 over the guidewire 60.

FIG. 8 shows one example of a structure for facilitating rotation of the bevel 150 of the needle distal tip 30B described above, wherein a housing 242 of the needle retraction assembly includes a needle hub 232 that is slidably disposed therein. Handles 244 of the needle hub 232 extend through the wall of the housing 242 to enable manual translation of the needle hub along the length of the housing. The internal portion the needle hub 232 is operably connected to a spiral track 250 defined by the inner wall of the housing 242, which enables the needle hub to rotate about its sliding axis as it is moved proximally within the housing. As a proximal end of the needle 30 is fixedly secured to the needle hub 32, rotation of the needle hub desirably causes corresponding rotation of the needle distal tip bevel 150, as seen in FIGS. 7A-7C. In addition to this, other structures for causing needle tip bevel rotation can also be employed in the insertion device.

Figure 9A:
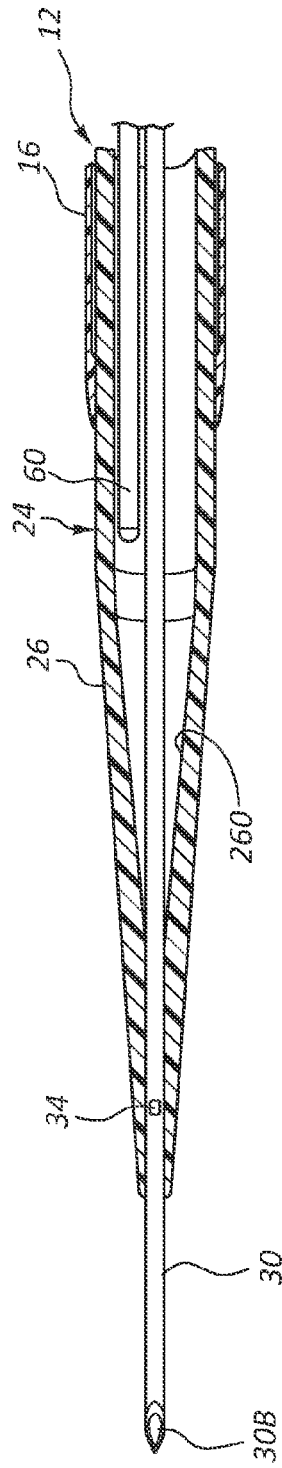
FIGS. 9A-9C show a distal portion of an insertion device according to one possible embodiment.
Figure 9B:
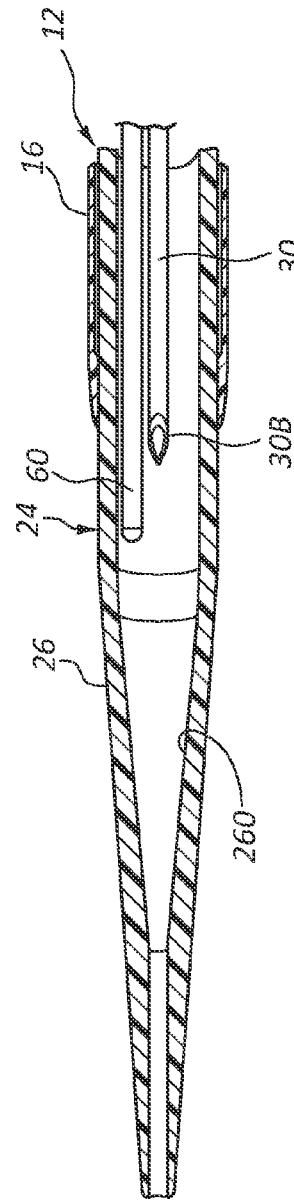
Figure 9C:
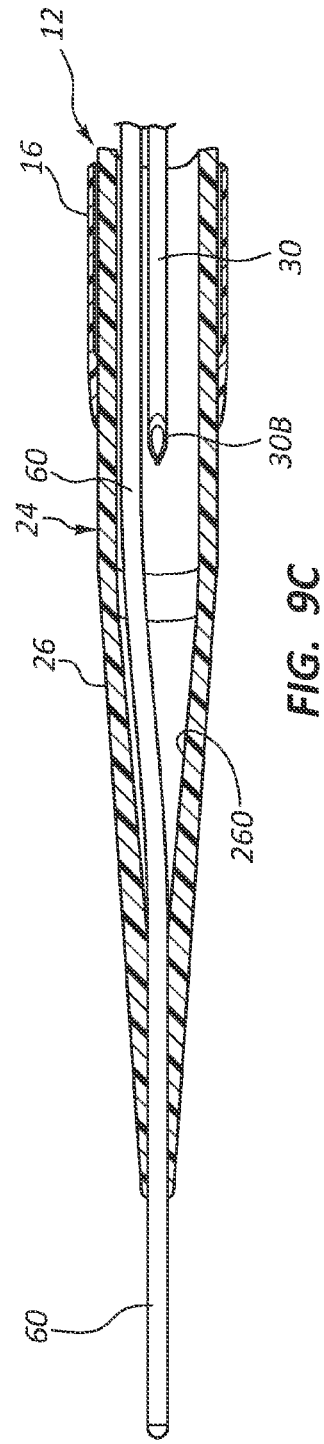

FIGS. 9A-9C show details of a distal portion of the insertion device according to one embodiment, wherein the guidewire 60 is not disposed within the hollow needle 30, but rather is disposed alongside the needle within the bore 260 of the dilator 20. Particularly, in FIG. 9A the needle 30 is shown extended in position 1, with the guidewire retracted within the dilator bore 260. In FIG. 9B, the needle is retracted into the dilator bore 260 in position 3. In FIG. 9C, the guidewire 60 is extended past the distal end of the dilator bore 260. The needle and guidewire configuration shown in FIGS. 9A-9C is useful for implementations where a guidewire that is larger than what would otherwise fit within the needle is desired to be used, or in cases where a relatively smaller needle is desired to be used so as to reduce patient discomfort and excess bleeding.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An insertion device for inserting an introducer assembly into a body of a patient, the introducer assembly including a sheath and a dilator coaxially disposed in the sheath, the dilator defining a bore, the sheath and dilator each having a hub, the sheath hub threadably engaging a distal end of the dilator hub, the insertion device comprising:
   a needle removably disposed within the bore of the dilator; and
   a retraction assembly including a housing in which a needle hub is disposed, the needle hub attached to a proximal end of the needle, the housing threadably engaging a proximal end of the dilator hub, the retraction assembly and dilator being removable from the sheath after placement thereof within the patient body is complete, the removal of the retraction assembly causing removal of the needle from the sheath, the retraction assembly capable of producing relative positions of the needle and the introducer assembly, the relative positions including:
   a first locked position wherein a distal tip of the needle is disposed a predetermined distance distal to a distal end of the introducer assembly,
   a second locked position wherein the needle distal tip is disposed proximal to the needle distal tip in the first locked position and distal but proximate to the distal end of the introducer assembly, and
   a third locked position wherein the needle distal tip is retracted within the dilator bore,
   the needle hub movably disposed in the housing to move the needle between the first, second, and third locked positions, the needle hub including at least one protruding feature to engage at least one recessed feature of the housing to releasably lock the needle hub and maintain the needle in each of the first, second, and third locked positions.

2. The insertion device as defined in claim 1, wherein the dilator includes a tapered distal portion, the distal tip of the needle in the second locked position providing a transition for the tapered distal portion.

3. The insertion device as defined in claim 1, wherein the needle is hollow for passage of a guidewire therethrough, the guidewire also passing through the retraction assembly housing, the guidewire able to remain with the introducer assembly after the retraction assembly and the needle are removed from the introducer assembly.

4. The insertion device as defined in claim 1, wherein the needle in the first locked position is used to gain needle access to an interior portion of the body of the patient, in the second locked position is used to assist a first distal portion of the introducer assembly to gain access to the interior portion, and in the third locked position is used to enable a second distal portion of the introducer assembly to gain access to the interior portion.

5. The insertion device as defined in claim 1, wherein the needle hub includes a distally extending handle to enable one-handed grasping of the insertion device and movement of the needle between the first, second, and third locked positions.

6. The insertion device as defined in claim 1, wherein the retraction assembly includes:
   a biasing element disposed within the housing of the retraction assembly, the biasing element configured for moving the needle between at least two of the first, second, and third locked positions;
   a guidewire; and
   a guidewire handle extending from the housing and configured to enable manual advancement of the guidewire.

* * * * *